US012564684B2

(12) United States Patent
Enderle et al.

(10) Patent No.: US 12,564,684 B2
(45) Date of Patent: Mar. 3, 2026

(54) INSTRUMENT, INSTRUMENT HEAD, APPLICATION SYSTEM AND METHOD

(71) Applicant: Erbe Elektromedizin GmbH, Tuebingen (DE)

(72) Inventors: Markus Enderle, Tuebingen (DE); Andreas Fech, Tuebingen (DE); Achim Brodbeck, Metzingen (DE)

(73) Assignee: Erbe Elektromedizin GmbH, Tuebingen (DE)

( * ) Notice: Subject to any disclaimer, the term of this patent is extended or adjusted under 35 U.S.C. 154(b) by 168 days.

(21) Appl. No.: 16/831,977

(22) Filed: Mar. 27, 2020

(65) Prior Publication Data

US 2020/0306450 A1      Oct. 1, 2020

(30) Foreign Application Priority Data

Mar. 28, 2019   (EP) ..................................... 19165793

(51) Int. Cl.
*A61M 5/30*            (2006.01)
(52) U.S. Cl.
CPC ....... *A61M 5/3007* (2013.01); *A61M 2202/09* (2013.01); *A61M 2206/18* (2013.01); *A61M 2210/1085* (2013.01)
(58) Field of Classification Search
CPC .... A61M 5/3007; A61M 5/30; A61M 5/1407; A61M 5/16827; A61M 5/16809;
(Continued)

(56) References Cited

U.S. PATENT DOCUMENTS 6,161,778 A    12/2000  Haruch
6,796,704 B1 *  9/2004  Lott ........................ B01F 25/10
                                                          366/165.2
(Continued)

FOREIGN PATENT DOCUMENTS

CN        101355982 A    1/2009
CN        102089083 A    6/2011
(Continued)

OTHER PUBLICATIONS

Notice of reasons for refusal (untranslated) Notice of reasons for refusal (translated).

*Primary Examiner* — Kevin C Sirmons
*Assistant Examiner* — Alexandra Lalonde
(74) *Attorney, Agent, or Firm* — Blank Rome LLP

(57)             ABSTRACT

An instrument with a first conduit for emitting a first fluid from a first opening of the first conduit in an axial direction into a reacceleration zone and with a second conduit for channeling of a second fluid in the reacceleration zone in the axial direction is provided such that active ingredient components, e.g. cells, of the second fluid are reaccelerated in the axial direction as a result of a flow in the reacceleration zone by means of the first fluid that enters the reacceleration zone. A coaxial configuration of the first and the second conduit is preferred, because in doing so, around the first opening a shell jet of the second fluid can be created that flows downstream in the axial direction around a central working jet. In addition, a head for an inventive instrument and an application system with an inventive instrument is provided.

13 Claims, 7 Drawing Sheets

(58) Field of Classification Search
CPC ............ A61M 5/2066; A61M 5/31596; A61M
5/2448; A61M 2206/18; A61M 11/02;
A61M 11/007; A61M 2005/1787; A61M
5/19; A61M 5/204; A61M 5/2053; A61M
5/284; A61M 3/0233; A61M 2025/0004;
A61M 2025/0006; A61M 2025/0039;
A61M 39/24; A61M 2039/2426; A61M
2210/1085; A61M 2202/09; A61B
17/3203; A61B 1/015; C12M 3/006;
B05B 7/061; B01F 25/31243
See application file for complete search history.

(56)                    References Cited

U.S. PATENT DOCUMENTS

| | | | |
|---|---|---|---|
| 7,914,484 B2 | 3/2011 | Yokoyama | |
| 9,573,147 B1 | 2/2017 | Yeates et al. | |
| 9,673,032 B1 | 6/2017 | Schleifer et al. | |
| 2009/0036824 A1* | 2/2009 | Tavger ................... A61M 5/30 | |
| | | | 604/24 |
| 2009/0270796 A1 | 10/2009 | Perry et al. | |
| 2009/0297410 A1 | 12/2009 | Lobet et al. | |
| 2011/0028887 A1* | 2/2011 | Fischer ............. A61B 17/3203 | |
| | | | 604/24 |
| 2011/0114266 A1 | 5/2011 | Petersen et al. | |
| 2012/0172874 A1 | 7/2012 | Fischer et al. | |
| 2012/0307588 A1* | 12/2012 | Hanada ................ B01F 25/312 | |
| | | | 366/336 |

| | | | |
|---|---|---|---|
| 2013/0144211 A1 | 6/2013 | Vogt et al. | |
| 2013/0331772 A1* | 12/2013 | Vogt ...................... B05B 7/2435 | |
| | | | 604/24 |
| 2014/0107683 A1 | 4/2014 | Kühner et al. | |
| 2016/0184524 A1* | 6/2016 | Fech ................... A61M 5/1407 | |
| | | | 604/500 |
| 2018/0353233 A1 | 12/2018 | Brodbeck et al. | |

FOREIGN PATENT DOCUMENTS

| | | |
|---|---|---|
| CN | 103815947 A | 5/2014 |
| CN | 105727424 A | 7/2016 |
| CN | 206896574 U | 1/2018 |
| CN | 206906092 U | 1/2018 |
| CN | 108654870 A | 10/2018 |
| CN | 108992163 A | 12/2018 |
| EP | 2 601 986 A1 | 6/2013 |
| EP | 2 851 129 A1 | 3/2015 |
| EP | 2 907 582 A1 | 8/2015 |
| EP | 3 040 036 A1 | 7/2016 |
| EP | 3 040 101 A1 | 7/2016 |
| EP | 3 412 234 A1 | 12/2018 |
| JP | 2015062733 A | 4/2015 |
| JP | 2016123863 A | 7/2016 |
| JP | 2018202176 A | 12/2018 |
| KR | 20160080074 A | 7/2016 |
| KR | 20160080078 A | 7/2016 |
| KR | 20180133802 A | 12/2018 |
| TW | 201436874 A | 10/2014 |
| WO | WO 99/17833 A1 | 4/1999 |
| WO | WO 2013/ 088086 A1 | 6/2013 |

* cited by examiner

INSTRUMENT, INSTRUMENT HEAD, APPLICATION SYSTEM AND METHOD

CROSS-REFERENCE TO RELATED APPLICATION

This application claims the benefit of European Patent application Ser. No. 19/165,793.1 filed on Mar. 28, 2019, the contents of which is incorporated by reference herein.

TECHNICAL FIELD

The invention refers to an instrument, particularly an instrument for applying a substance in body tissue, an instrument head, an application system as well as a method.

BACKGROUND

In the methods for injecting a substance in tissue known from the prior art an injection cannula paired with a disposable syringe can be used. The injection cannula (cannula) can comprise, e.g. a diameter of up to 1.6 mm. An increased risk of an insufficient positioning, as well as the danger of perforation of the tissue at an undesired location exists for the manual application and injection of a substance with an injection needle. In addition, a comparable large tissue traumatization occurs at the penetration location, due to the large diameter of the cannula (up to 1.6 mm). Further, a large penetration or opening channel results in that a large amount of the introduced substance can exit from the tissue and thus valuable material can get lost. Besides the loss this can also lead to an increased accumulation of the substance in tissue areas outside of the target area. Damage of a muscle, due to the penetration that can lead to scarring of healthy muscle tissue (fibrosis) is a further disadvantage, particularly if with one needle per puncture only a small volume of the substance can be output in a spatial largely limited area and thus, e.g. a circumferential circular treatment of the sphincter requires several punctures. Besides the increased need of time in doing so, also the effectivity of the treatment decreases, because here an additional effect is created in the muscle that in the worst case increases the regeneration effect of the therapy by the substance. This aspect gains in importance in view of the relatively large cannula diameter of up to 1.6 mm.

EP 3 040 036 A1 proposes an approach for a needleless introduction of cells by means of a water jet. The proposed instrument allows a spatial and timely separated supply of two substances, such that for example a sequential application of the cells and the carrier medium is possible.

EP 3 040 101 A1 proposes a pump or dispensing system that allows a sequential application with different amounts of pressure levels.

EP 2 907 582 A1 discloses a device for spraying of medical fluids in overlapping spraying cones.

During the application of cells the shear forces applied thereon can damage the cells. A concept would be advantageous for a needleless injection of a substance, particularly of active ingredients, particularly cells, in which the functioning of the active ingredients is mainly maintained, particularly the damage of the cells that have to be inserted is mainly avoided.

SUMMARY

This object is solved with example instruments, instrument heads, application systems, and methods as disclosed herein.

The inventive instrument comprises a first conduit for output of a first fluid from a first opening of the first conduit in an axial direction in a reacceleration zone. In addition, the instrument comprises a second conduit for channeling a second fluid in the reacceleration zone in the axial direction such that at least portions of the second fluid as a result of the flowing of the first fluid in the reacceleration zone are reaccelerated in the axial direction by the first fluid entering the reacceleration zone. The first fluid can also be named as a working fluid. The second fluid can also be named as active ingredient fluid and can comprise cells that shall be applied in the body tissue by means of the instrument.

When entering the reacceleration zone, the second fluid, particularly the ingredients thereof that are to be reaccelerated, already have a velocity component in the axial direction. The relative velocity in the axial direction between the first fluid for reaccelerating the ingredients of the second fluid and the ingredients of the second fluid is thus smaller than the velocity of the first fluid. Thus the ingredients, e.g. cells, are subject to smaller velocities, pressures, velocity and pressure differences and as a consequence also to reduced shock and shear stresses such that they can be conveyed remarkably more carefully into the tissue.

Additional advantageous features of the inventive instrument, the inventive instrument head, the inventive application system and the inventive method are derived from the following description.

Preferably the second conduit comprises a preacceleration zone upstream of the reacceleration zone. The instrument is preferably configured to preaccelerate the second fluid in the preacceleration zone in the axial direction. The first opening is arranged at the reacceleration zone such that the first fluid output from the first opening reaccelerates the preaccelerated second fluid in the axial direction. By means of the preacceleration zone the second fluid can be brought to an increased velocity only shortly before the reacceleration zone in order to reduce the relative velocity between the first fluid and the second fluid at the beginning of the reacceleration zone. A preacceleration zone upstream of the reacceleration zone adjacent to the distal end of the instrument has the advantage that the second fluid can be supplied up to the preacceleration zone adjacent to the distal end of the instrument with low velocity and that the second fluid is only preaccelerated adjacent to the distal end of the instrument, e.g. in an instrument head.

The preacceleration zone is preferably formed by a nozzle section of the second conduit, in which the flow cross-section area of the second conduit tapers in flow direction (axial direction). The ratio of the velocity in a cross-section to the velocity in a tapered cross-section is as known proportional to the ratio of the tapered cross-section area to the cross-section area.

A pressure pulsation of the second fluid in and/or after the nozzle section is mainly avoided, if the cross-section continuously tapers in at least one subsection of the nozzle section.

Preferably the second conduit surrounds the first conduit at the first opening concentrically in order to form a ring-shaped shell jet of second fluid around the fluid exiting from the first opening. This improves the uniform loading of the surface of the jet of the first fluid with ingredients from the second fluid.

Preferably the second fluid is configured to guide the shell jet radially close to the first conduit such that the working jet, that is output from the first opening, sucks ingredients of the shell jet into the working jet. This effect can be traced back to the Bernoulli effect, because of the initially higher velocity of the working jet relative to the shell jet.

Preferably the outer wall of the second conduit is elastic in a section around the first opening. This leads to a self-centering of the second conduit around the first opening, e.g. in order to balance comparably large tolerances within which the second conduit concentrically surrounds the first conduit at the first opening.

The section can be formed by an elastic element that also forms the nozzle section completely or partly. A self-centering can thus be carried out in the nozzle section.

Preferably the elastic element is fluidically connected upstream with a tube section of the second conduit. A centering device can be effective radially between the tube section and the first conduit. The tube section is rigid and/or inflexible, at least for the pressures and forces that usually occur during normal operation. This finally improves the formation of a ring-shaped shell jet of second fluid around the carrier jet of first fluid.

The tube section of the second conduit that is inflexible in radial direction, preferably surrounds a tube section of the first conduit that is inflexible in radial direction, wherein the centering device can be arranged between the tube section of the second conduit and the tube section of the first conduit, in order to concentrically align the tube section of the first conduit and the tube section of the second conduit.

Preferably the reacceleration zone, in which also the introduction of ingredients of the second fluid in the carrier jet occurs, is formed within the instrument. The instrument preferably provides for the carrier jet with ingredients of the second fluid exiting through the distal opening from the instrument downstream of the reacceleration zone.

For example, the distal opening of the instrument may be placed on the tissue. An injection channel can be introduced into the tissue by means of the instrument in a needleless manner with a pilot jet of first fluid.

The second conduit ends preferably downstream of the first opening. In other words, the second conduit preferably surrounds at least a section of the reacceleration zone. As a result the flow of the second fluid in the reacceleration zone remains in a predefined shape and does not excessively diverge outwardly. The second conduit is preferably cylindrical in the section protruding beyond the first opening. This improves the transfer of ingredients of the second fluid on the carrier flow or carrier jet.

The second conduit ends preferably upstream of the distal opening of the instrument. Therefore, also, if the end section of the instrument that is preferably rigid in compression is placed with the distal opening on the tissue, the tissue does not reach the distal end of the second conduit and thus does not press onto the second conduit. In doing so, the second conduit is not unintentionally deformed, particularly if it comprises an elastic conduit element at the distal end.

The instrument is preferably configured to channel the first fluid and the second fluid adjacent to each other toward the vicinity of the distal end of the instrument in conduit sections that are arranged adjacent to each other, preferably parallel to each other. The instrument is preferably also configured to subsequently channel the first fluid and the second fluid further in direction toward the distal end in coaxial conduit sections.

Preferably the preacceleration zone and/or the reacceleration zone are arranged in a head of the instrument. In doing so, the second fluid only flows along a small distance between the preacceleration zone and/or the reacceleration zone and the distal end of the instrument. Damages of the cells due to the transport over longer distances and with higher velocities are thus avoided.

The head of the instrument is preferably replaceable.

According to the invention also an instrument head for an instrument is provided. It comprises preferably the preacceleration zone and/or the reacceleration zone. The instrument head is preferably attachable at proximal conduit sections of the first and second conduit in a replaceable manner.

In addition, an application system with any of the embodiments of the inventive instrument is provided. In addition, the application system comprises a supply device that is fluidically connectable with the first conduit and the second conduit and that is configured to supply the first fluid and the second fluid in a sequence of supply intervals.

Preferably the supply device comprises a control that controls the application system such that within one application time interval during a first working fluid supply interval, the first fluid is supplied such that it comprises a first velocity at the first opening for forming a channel in the tissue. In addition, the control controls the application system such that during a second working fluid supply interval, the first fluid is supplied such that it comprises a reduced first velocity at the first opening that is smaller than the first velocity. In addition, the control controls the application system such that at least in phases during the second working fluid supply interval, the second fluid is supplied such that the second fluid comprises a second velocity at the first opening that is smaller than the reduced first velocity.

The inventive method for application of an active ingredient, particularly cells, in body tissue comprises a step of the needleless opening of a channel in the tissue by means of a working jet of first fluid emitted from a first conduit out of a first opening of an instrument. The instrument is preferably an inventive instrument as described herein, particularly according to any of the embodiments described above. In a second step a jet of a second fluid is output from a second conduit of the instrument parallel or coaxially to the working jet. The second fluid comprises ingredients, particularly active ingredients such as cells that are accommodated from the working jet and carried into the channel. The ingredients are preferably accommodated by suction of the second fluid from the jet of the second fluid in the working jet. Between the first step and the second step the output or creation of the working jet can be interrupted. Preferably the working jet is only weakened for the second step and can be particularly emitted with lower velocity compared with the velocity for the opening of the channel in the tissue. Apart therefrom the working jet can be output without interruption during the first and second step. In doing so, it can be guaranteed that the channel created by the working jet is maintained open by the working jet.

BRIEF DESCRIPTION OF THE FIGURES

Further optional preferred features and embodiments can be derived from the following description as well as the drawings. The drawings show:

FIG. 1a—a highly schematically illustrated embodiment of the inventive instrument in a partly longitudinal section, FIG. 1b—a view of a cross-section of the embodiment according to FIG. 1a for illustration of a self-centering effect, FIG. 2—a further embodiment of the inventive instrument in a longitudinal section, FIG. 3a—an enlarged view of a section drawn in FIG. 2 of the instrument according to the embodiment of FIG. 2, FIG. 3b—a sectional view of an area of a sectional plane through FIG. 3a, FIG. 3c—a cross-section of the instrument along the cutting line B-B illustrated in FIG. 3, FIG. 4—a detailed view of a section that is illustrated in FIG. 2, FIG. 5a—a highly schematic view of an embodiment of the inventive application system, FIG. 5b—a section of FIG. 5a, FIG. 6—diagrams for illustration of a time sequence of a control of the application system according to FIG. 5a.

DETAILED DESCRIPTION

Figure 1A:
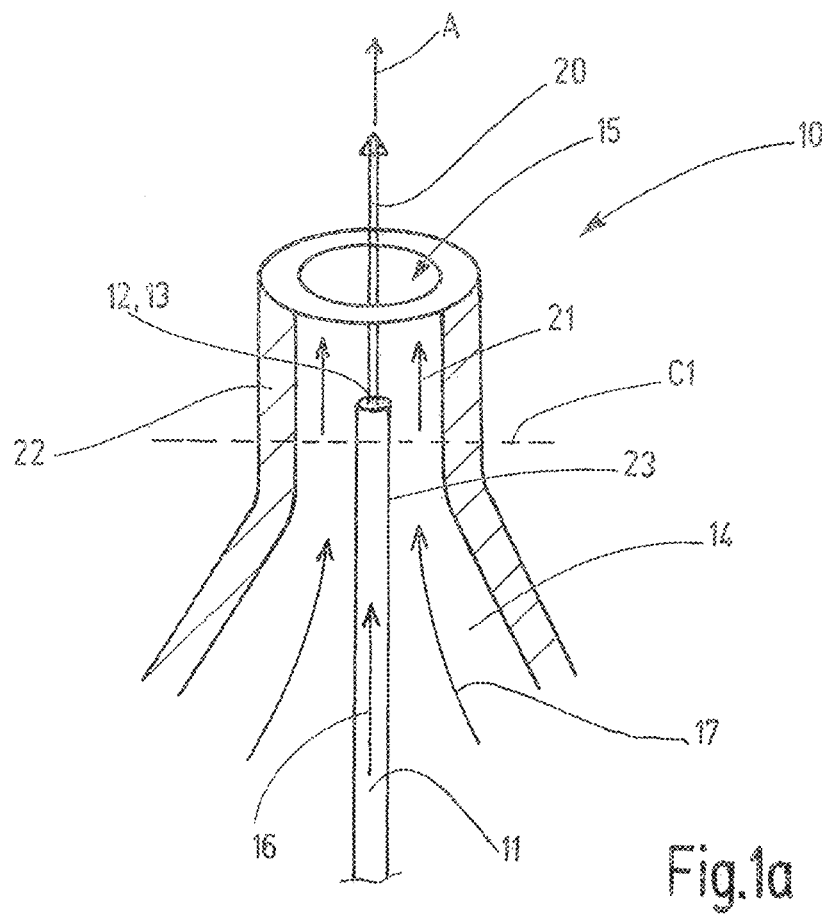

FIG. 1a highly schematically illustrates an inventive instrument 10 with a first conduit 11 having a first opening 12 at the face 13 of the first conduit 11. The first conduit 11 is arranged in a second conduit 14. In the embodiment the first conduit 11 forms an inner wall 27 of the second conduit 14. The first conduit 11 and the second conduit 14 are arranged coaxially. The first opening 12 is arranged upstream an opening (second opening 15) of the second conduit 14. Through the first conduit 11 a first fluid 16 and through the second conduit 14 a second fluid 17 can flow in the axial direction A. As illustrated, the inner cross-section of the second conduit 14 provided for the second fluid 17 tapers in the axial direction A toward the second opening 15. In doing so, the second fluid 17 channeled inside the second conduit 14 can be preaccelerated before it passes the first opening 12 in the axial direction A and gets into contact with the first fluid 16 output from the first opening 12 in the axial direction A. The section with the tapering inner cross-section forms a preacceleration zone 18. The area downstream of the first opening 12 can be referred as reacceleration zone 19, because in this zone ingredients of the second fluid 17 are received in the carrier flow 20 of the first fluid 16 in order to be introduced by the carrier flow 20 in the tissue of a patient. Due to the coaxial configuration, the fluid flow of the second fluid 17 forms a shell flow 21 around the carrier flow 20. This improves transfer of ingredients of the second fluid 17 into the first fluid 16 at all circumferential locations. For this the normal vector of the opening surface of the first opening 12 that is surrounded by the opening surface of the first conduit 11 is preferably orientated parallel to the axial direction A. This configuration preferably also applies to the embodiments that are explained with reference to FIGS. 2 to 4. If the face side first opening 12 at the first conduit 11 is orientated in the axial direction, this supports the uniform loading of the working jet or working jet 20 with ingredients, particularly cells, substantially directly after the exit from the first conduit 11.

Figure 1B:
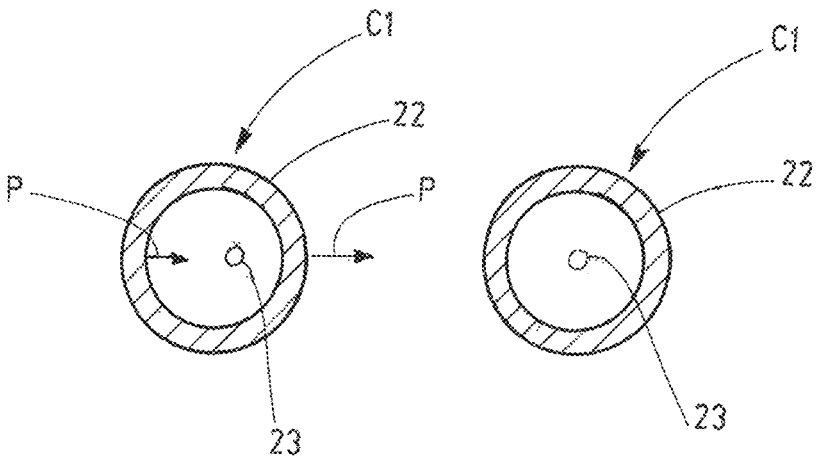

Preferably an outer wall section 22 of the second conduit 14 at least in the area of the first opening 12 is flexible, preferably elastically flexible. This leads to a self-centering effect of the flexible section 22 around the first opening 12. This is particularly schematically illustrated in FIG. 1b. Here a cross-section view of the instrument 10 according to FIG. 1a is illustrated (cross-section area B is shown in FIG. 1a). As it is apparent, the flexible (preferably elastic) section 22 is not concentrically arranged around a nozzle tube 23 that forms the distal end of the first conduit 11. This can occur due to large tolerances. It has to be noted that FIGS. 1a and 1b are not true to scale. If the second conduit 14 is pressurized with the second fluid 17, the flexible axial outer wall section 22 that is represented by the outer ring-shaped cross-section area is moved and centered by the second fluid in radial direction as schematically illustrated by arrows P in FIG. 1b (right side illustration). The first conduit 11 thereby remains in the initial position. This is decisive, because in a first step a channel can be open in the tissue by means of the first conduit 11 and a fluid pulse from the first conduit 11 in a needleless manner. In a second step the ingredients can be introduced in this tissue channel by means of the carrier flow 20. If the fluid flow of second fluid 17 is interrupted, the ring-shaped outer wall section 22, as far as it is elastic, will automatically return in its initial position (FIG. 1b left side illustration). Also embodiments can be realized in which an elastic ring-shaped outer wall section of the second conduit comprising a self-centering characteristic can be omitted.

Figure 2:
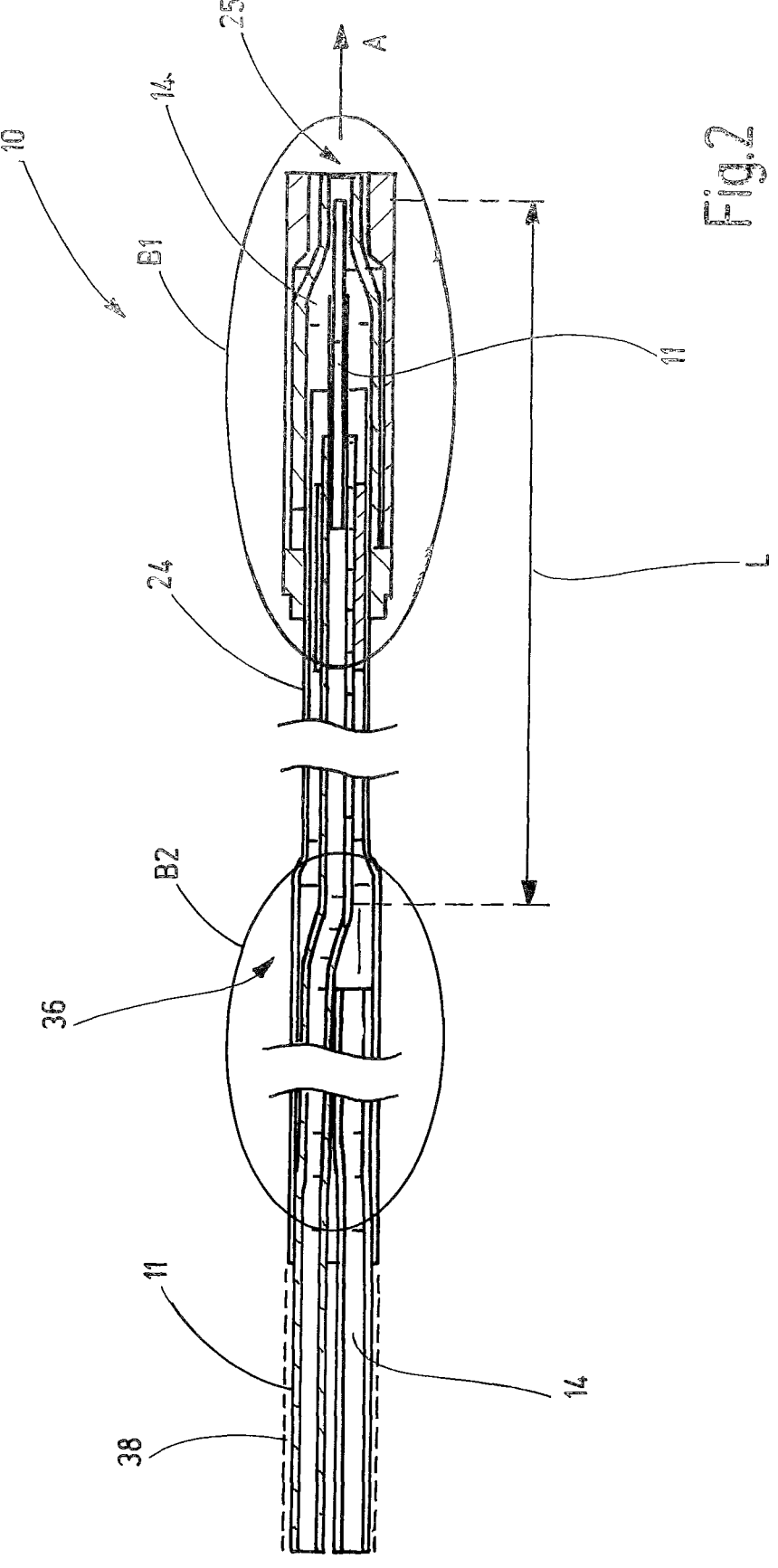

FIG. 2 shows a longitudinal section view in portions of a further embodiment of an inventive instrument 10. The instrument 10 can be usable for an open endoscopic or laparoscopic intervention. Particularly the instrument 10 can be a catheter instrument 10, which can be inserted into the urethra in order to carry out a treatment of the bladder's sphincter by introduction of cells therein. Thus, by means of the same instrument 10, a channel can be created through outer layers of the sphincter in the muscle tissue in a needleless manner and liquid comprising cells can be injected in a needleless manner.

The instrument 10 comprises a longitudinally extended head 24 at the distal end 25 of the instrument 10. The head 24 is inflexible and/or rigid. A section of the conduit pair defined by the sections of the conduits 11, 14 up to the head 24 is flexible. In the head 24 the first conduit 11 is concentrically arranged to a second conduit 14. As it is apparent particularly from FIG. 3, the first conduit 11 comprises a configuration of multiple conduit sections that form inner cross-section stages. The inner cross-section is reduced toward the distal end or in the axial direction in a stepwise manner. The end of the first conduit 11 is formed by a nozzle tube 23. Also from the proximal conduit section 26 to the nozzle tube 23 the inner cross-section of the first conduit 11 decreases such that the first fluid is subject to an acceleration during the passage through the first conduit 11. The reduction of the inner cross-section and thus preferably also the outer cross-section of the first conduit 11 in this region serves, however, not primarily to the acceleration of the first fluid. Embodiments can also be realized without the reduction of the conduit cross-section of the first conduit 11 at the distal end. Rather, due to the reduction of the inner and outer cross-section, a high stability of the nozzle tube 23 in the distal region and also a lesser reduction of the inner cross-section of the second conduit 14 can be achieved. A diameter reduction is particularly advantageous that comprises continuous and/or uniform diameter transitions (different to the illustration according to FIG. 2 or 3). Such a nozzle tube 23 with continuous reduction of the inner cross-section in the axial direction for the first conduit 11 can be, e.g. manufactured as an integral part, for example by forging or swaging of a cylindrical tube, particularly rotary swaging. In doing so, also the nozzle opening (first opening 12) can be created in the nozzle tube 23.

In the head 24 the second conduit 14 comprises an outer wall that is formed by at least two elements. The inner wall is formed by the outer wall 27 of the first conduit 11 such that a ring-shaped conduit cross-section (inner cross-section) of the second conduit 14 is obtained in the head 24 of the instrument 10. A rigid shaft tube section 28 of the second conduit 14 of uniform diameter is connected at the distal end thereof with an elastic outer wall element 29 that forms a nozzle 30 of the second conduit 14. The elastic outer wall element 29 is shifted on the distal end of the shaft tube 28. The elastic outer wall element 29 comprises a cylindrical section 29*a*, a tapering section 29*b* adjoining thereto, as well as a further cylindrical section 29*c*. The further cylindrical section 29*c* could alternatively be a section that tapers in the axial direction A, e.g. conically.

The nozzle tube 23 opens out with a first opening 12 in the further cylindrical section 29*c* of the elastic outer wall element 29 that is circumferentially closed. A coaxial arrangement of the first nozzle tube 23 and the outer nozzle 30 formed with the elastic outer wall element 29 is created. The outer nozzle 30 for the cell suspension comprises a conduit cross-section in the form of a ring gap 31 and is arranged concentrically with the nozzle tube 23 such that the ring gap 31 surrounds the nozzle tube 23. The conduit cross-section of the ring gap 31 decreases in the axial direction.

If now a second fluid, particularly a cell-containing suspension (cell suspension) flows through the outer nozzle 30, the second fluid is subject to a preacceleration adjacent to the distal end 25 of the instrument 10 due to the decreasing cross-section of the second conduit 14. Therefore, a preacceleration zone 18 is formed by the outer nozzle 30. Preferably the acceleration is, however, smaller than the acceleration of the working fluid during passage through the first nozzle tube 23. In each case the (average) exit velocity of the cell suspension after passage through the nozzle (on the level or adjacent to the first opening 12) is smaller than the (average) exit velocity of the working jet in the first opening 12. In a particularly preferred embodiment the ring gap shaped outer nozzle 30 for the cell suspension is dimensioned such that the nozzle exit velocity (adjacent to the first opening 12) of the cell suspension has an amount of 50-90% of the nozzle exit velocity of the working jet (in the first opening 12) under the condition of predefined volume flow rates or mass flow rates of the working liquid as a first fluid, e.g. of 5-55 ml/min and particularly of 15-26 ml/min and of the cell suspension of 1-30 ml/min and particularly of 15-26 ml/min. This applies for the phase, in which the emission of the cell suspension through the outer nozzle 30 and of the working fluid through the first opening 12 is carried out concurrently in order to insert cells from the cell suspension by means of the working fluid in a channel in the tissue. For the creation of the channel by means of a pilot jet of the working fluid the nozzle exit velocity of the working jet can be even higher.

It is particularly advantageous, if the ring gap 31 of the section of the second conduit 14 at the first opening 12 has an inner circumference U of at least 20 times of the average cell diameter of the cells in the cell suspension and a radial gap width b of at most ten times or event at most five times of the average cell diameter—however preferably at least four times of the average cell diameter. FIG. 3*b* shows a section along the section plane C3 that is drawn in FIG. 3*a*. In FIG. 3*b*, however, only the area of the section plane C3 around the center of the first opening 12 radially to the outer circumferential surface of the cylindrical section 29*c* of the flexible outer wall element 29 is shown. The inner circumference U of the ring gap 31 is equal to the outer circumference of the first nozzle tube 23. If the amount of the outer diameter of the first nozzle tube 23 is, e.g. 0.25 mm and thus the inner circumference U of the ring gap is about 0.79 mm, the ring gap 31 has, for example, a width b (radial gap width) of 0.1 mm, wherein a cell suspension with an average cell diameter of 25 micrometers is assumed. In doing so, on one hand the acceleration of the cell suspension is achieved as described above. On the other hand, tests have shown that in doing so, the ring gap 31 is dimensioned sufficiently large in order to allow a sufficiently unobstructed passage of the cells, if cells are used with an average diameter of 25 micrometers. The outer diameter of the working fluid jet (carrier jet) at the exit from the first opening 12 corresponds apart from two times the wall thickness of the nozzle tube 23 to the inner diameter of the ring gap 31 at the first opening 12. By formation of the shell jet or shell flow 21 of cell suspension a shell jet or shell flow around the working fluid jet or working fluid flow 20 is created (compare FIG. 1), in which the cells nearby the working fluid flow 20 enter next to the first opening 12, due to the radial dimension of the ring gap 31. In doing so, a particularly high accommodation of cells in the working fluid flow 20 can be guaranteed.

Figure 3A:
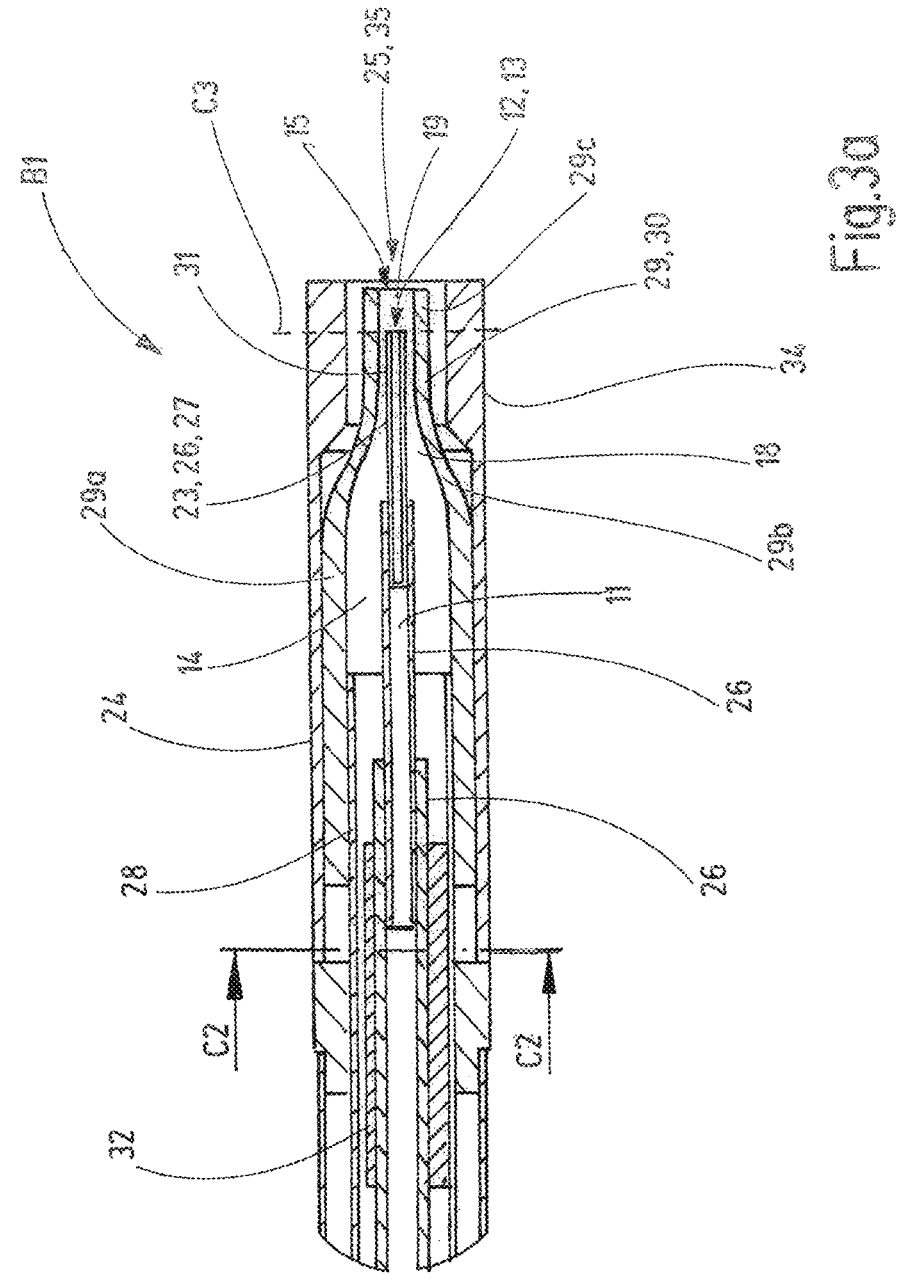
Figure 3B:
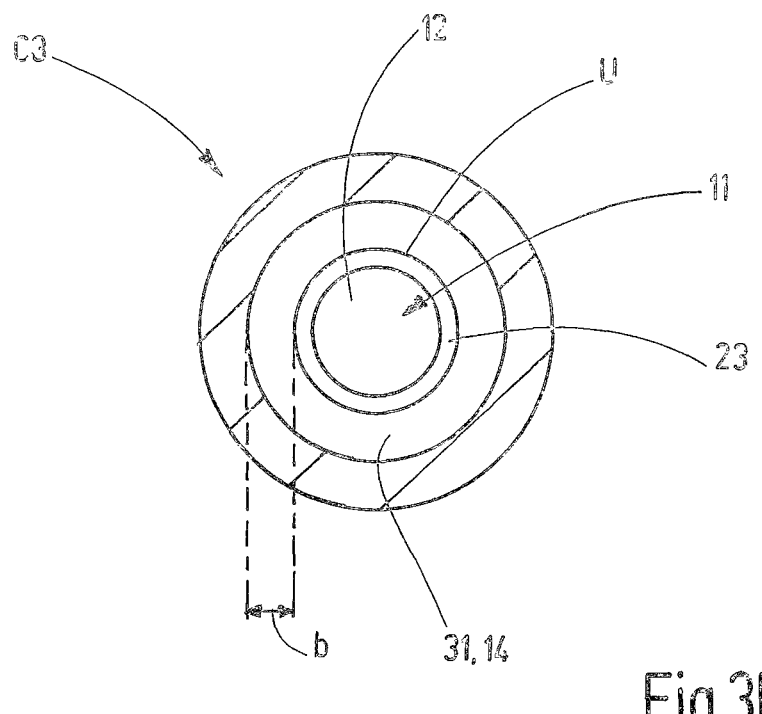
Figure 3C:
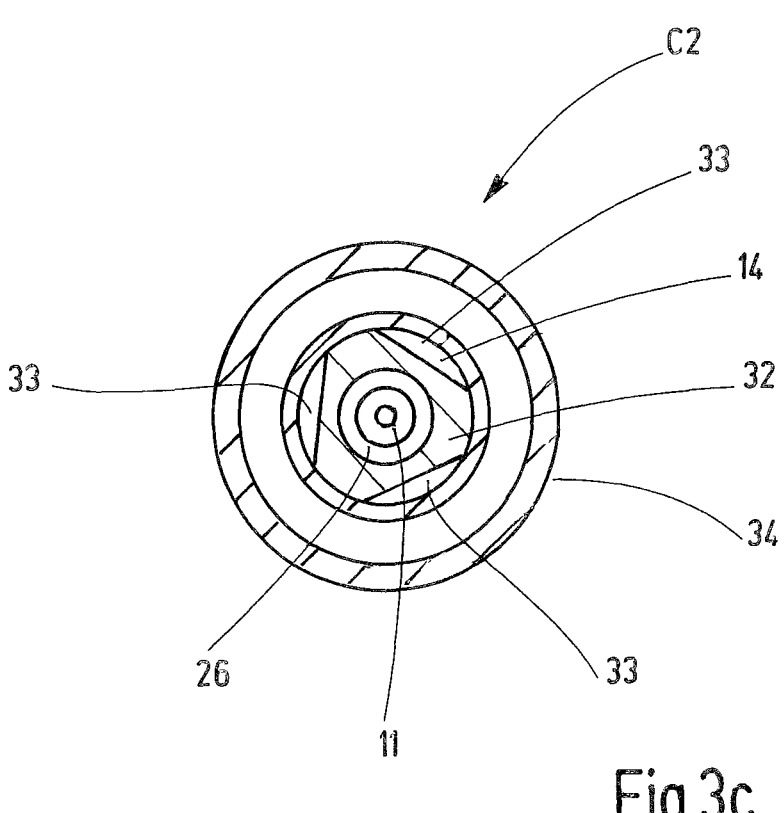
Figure 14:
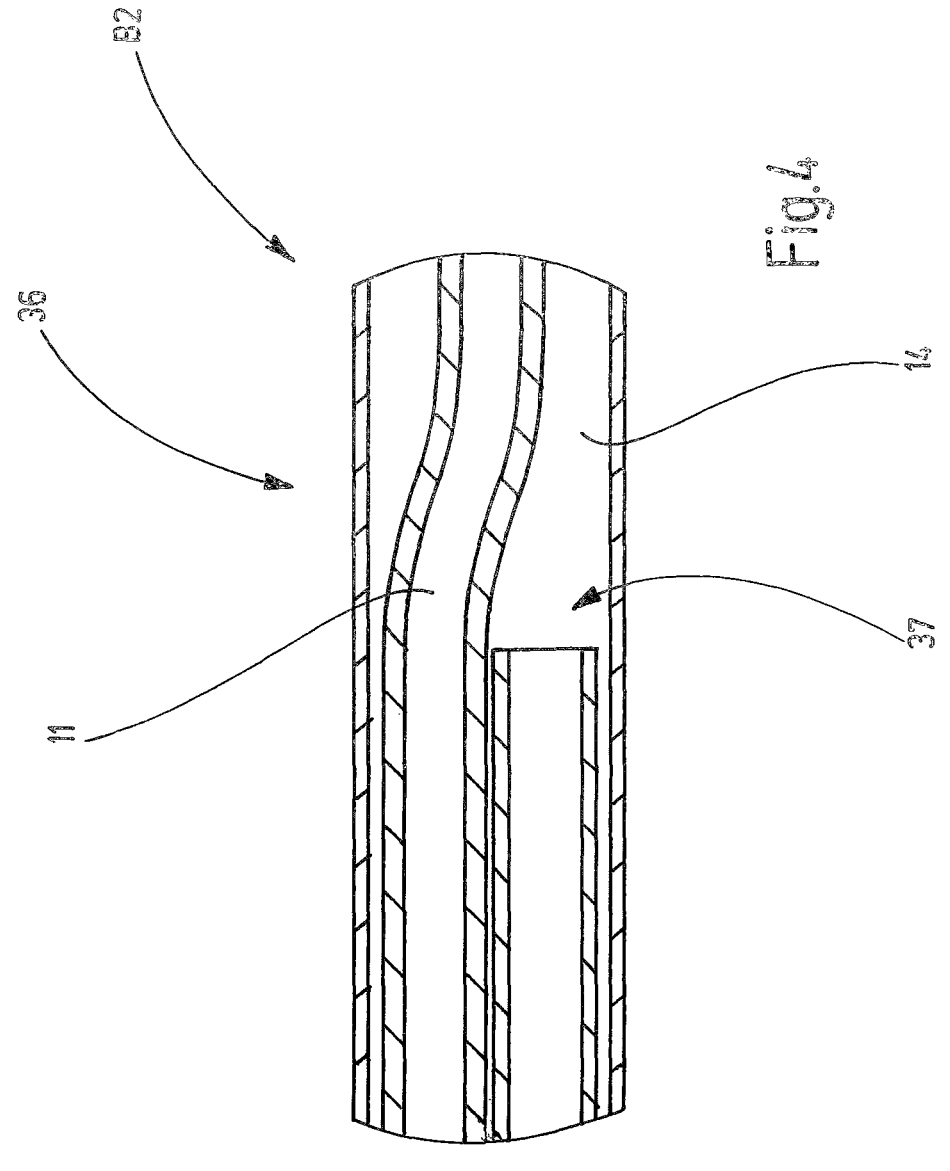

Between the rigid shaft tube section 28 and the first conduit 11 a centering element 32 is arranged, as is also apparent from FIG. 3*c*. The centering element 32 allows a fluid passage through the second conduit 14, even though it is arranged in the second conduit 14. The centering element 32 provides a coaxial arrangement of the shaft tube 28 and the first conduit 11. The centering element 32 comprises one or more recesses or clearances 33 that are open in the axial direction, e.g. in the form of longitudinal grooves on the outer shell surface of the centering element 32. The cell suspension can pass through the recesses 33. The recesses 33 comprise preferably a uniform cross-section. Preferably the recesses are distributed regularly around the circumference of the centering element 32. The centering element 32 finally provides a concentric arrangement of the first nozzle tube 23 for the working fluid 16 and the elastic outer wall element 29 for creation of the shell jet or shell flow 21. The centering element 32 creates the concentric arrangement of the first nozzle tube 23 with the elastic outer wall element 29 indirectly via the shaft tube 28, as illustrated in the embodiment according to FIG. 2.

The selected elastic resilience of the elastic element, by using a material with selected hardness and shape, can create a self-centering and adjusting effect of the converging outer nozzle, particularly the ring gap 31, during the passage of the cell suspension through the outer nozzle as it has been explained with reference to the embodiment according to FIG. 1*a* and particularly based on FIG. 1*b*. An asymmetry of the ring gap 31 that may remain, e.g. due to manufacturing tolerances, is compensated by applying a force on the elastic outer wall element 29 during the application of the cell suspension via the cell suspension flow. In doing so, the outer wall element 29 is deflected such that a symmetric ring gap 31 is created. The outer wall element 29 consists preferably of a biocompatible and for short-term (up to 25 hours) non-toxic elastic material, e.g. an elastomer as silicon or a thermoplastic elastomer. The thickness of the elastic outer wall element 29 comprises, for example, 0.05 to 1 mm, preferably 0.1 to 0.4 mm. The material hardness is in the range of 3 Shore (A) to 70 Shore (A) preferably in the range of 20 Shore (A) to 55 Shore (A).

The elastic outer wall element 29 is surrounded by a cap 34 that is compression resistant in the axial direction. The cap 34 forms the distal end 25 of the instrument 10. The cap 34 comprises an opening 35 at the distal face of the cap 34. The opening 15 at the face of the elastic outer wall element 29 (that is the second opening 15 at the face of the second conduit 14) opposite to the opening 35 of the cap 34 is proximally offset along the axial direction A. The face of cap 34 forms the distal end 25 of the instrument 10. The instrument 10 is configured compression resistant by means of the cap 34 that a minimum distance between the distal opening 35 of the instrument 10 that can be pressed on the tissue of the patient and the first opening 12 and/or the second opening 15 is maintained, even if pressure is applied on the distal end 25 of the instrument 10 during pressing the instrument 10 against the tissue. By the centering element 32 also the position of the first conduit 11 relative to the cap 34 is defined. This has the advantage that if the instrument 10 is placed with a cap 34 on the tissue and a channel is opened in the tissue by a fluid thrust from the first conduit 11, the first opening 12 remains above the such created channel such that a subsequent jet or flow from first fluid 16 with ingredients of the second fluid 17 reliably hits the channel.

FIG. 4 shows the portion B2 of FIG. 2 in an enlarged manner. As particularly and exemplarily apparent from FIGS. 2 and 5, the first conduit 11 and the second conduit 14 are preferably guided adjacent to each other, particularly parallel to each other near the distal end 25 of the instrument 10. Subsequently, further in the axial direction A toward the distal end 25 the first conduit 11 and the second conduit 14 are preferably arranged coaxially. In the embodiment the first conduit 11 and the second conduit 14 are arranged next to each other in the head 24 and following a transition location 36 in the head 24 coaxially to each other. At the transition location 36 the arrangement changes from the parallel to the coaxial arrangement by means of a switch arrangement. The transition location 36 can also be located upstream adjacent to the head 24 such that the first conduit 11 and the second conduit 14 are arranged adjacent to each other until near the head 24, e.g. twisted or parallel, and in flow direction or the axial direction A behind the transition location 36 toward the distal end 25 downstream and in the head 24 coaxially. Proximal or upstream of the transition location 36 or proximal of the head 24 the adjacent and particularly parallel first conduit 11 and second conduit 14 can be combined by means of a cladding hose 38. The cladding hose 38 is exemplarily illustrated with dashed lines around the first conduit 11 and the second conduit 14 in FIG. 2. The cladding hose 38 can, e.g. extend (as illustrated) in or over the head 24.

The transition from the parallel to the concentric channel arrangement or conduit arrangement can be created, e.g. by means of a switch arrangement 37 as it is exemplarily illustrated in FIG. 3. Of course, the first and second conduits 11, 14 illustrated separately adjacent to each other in FIGS. 2 and 4 can also be realized by one conduit body with separate and particularly parallel channels that are arranged adjacent to each other. The stress of the cells during passage through the channel in the area of the parallel channel arrangement is potentially lower as in the coaxial arrangement under the assumption of equal flow cross-sections, independent from whether two individual conduits 11, 14 or two channels contained in one conduit body are provided. This is because the coaxial arrangement of the inner and outer channel could be obtained by many centering elements in the ring space between the inner and outer conduit—this would however create increased shear forces at the centering element—or the securing of the coaxial arrangement could be omitted such that the inner conduit, particularly under bending or kinking, could abut inside at the outer conduit. Nonetheless, by the concentric channel arrangement in the area following the transition location 36 the already mentioned preferred configuration of a shell-like coating of the fluid flow 20 of cell suspension is achieved, wherein the fluid flow 20 is emitted from the first opening 12. It has been recognized that due to the short area between the transition location 36 and the distal end 25 of the instrument 10, in which the cell suspension due to the coaxial configuration flows through the ring cross-section, damage of the cells is minimized during passage of the second conduit 14 in the coaxial area. It has been particularly shown that at a length L of the coaxial area (from the transition location 36 to the first opening 12) of less or equal than 40 mm, no effect of the cell vitality was recognized. The centering device by means of centering element 32 that was explained with reference to FIG. 3a can alternatively be omitted. For example, if at a location at which the first conduit 11 is anyway arranged near the wall of the head 24, as illustrated in FIG. 4, the first conduit 11 can be fixed and particularly welded to the wall of the head 24 that may form the second conduit 14 downstream of the switch arrangement 37 (that is downstream of the transition from the parallel arrangement of the first conduit 11 and the second conduit 14 to the coaxial arrangement).

Figure 5A:
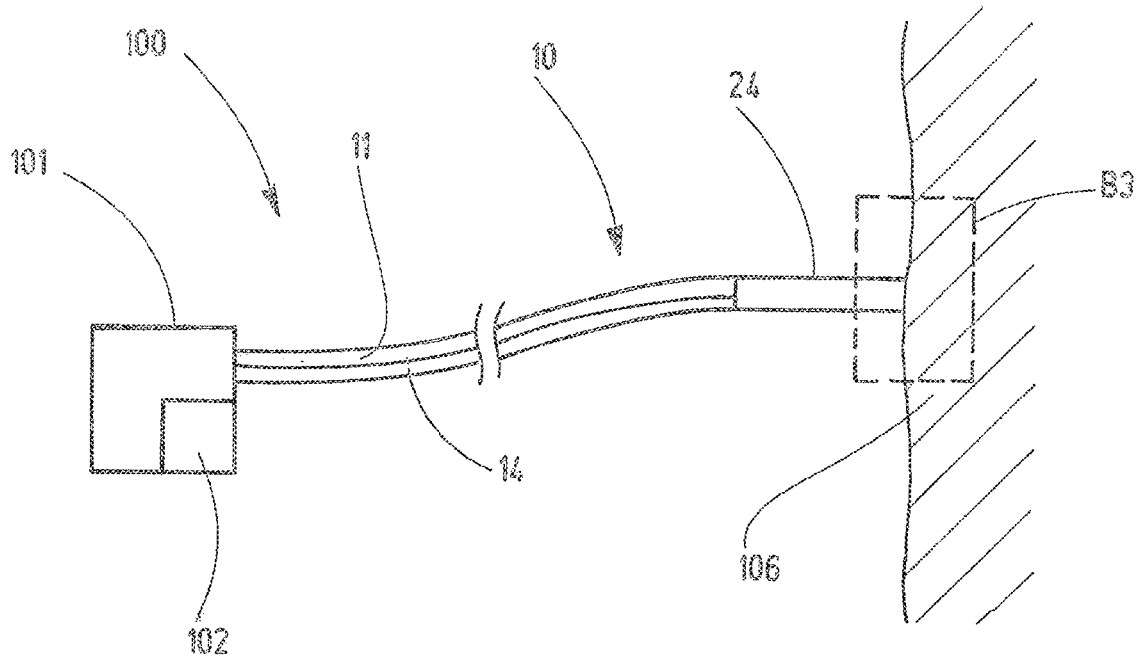

FIG. 5a highly schematically illustrates an embodiment of an application system 100 comprising an inventive instrument 10, e.g. an inventive instrument 10 according to one of the embodiments explained above. The system 100 additionally comprises a supply device 101 with a control 102 for control of the supply device 101. The supply device 101 comprises a source 103 for first fluid 16 and a source 104 for second fluid 17.

Figure 5B:
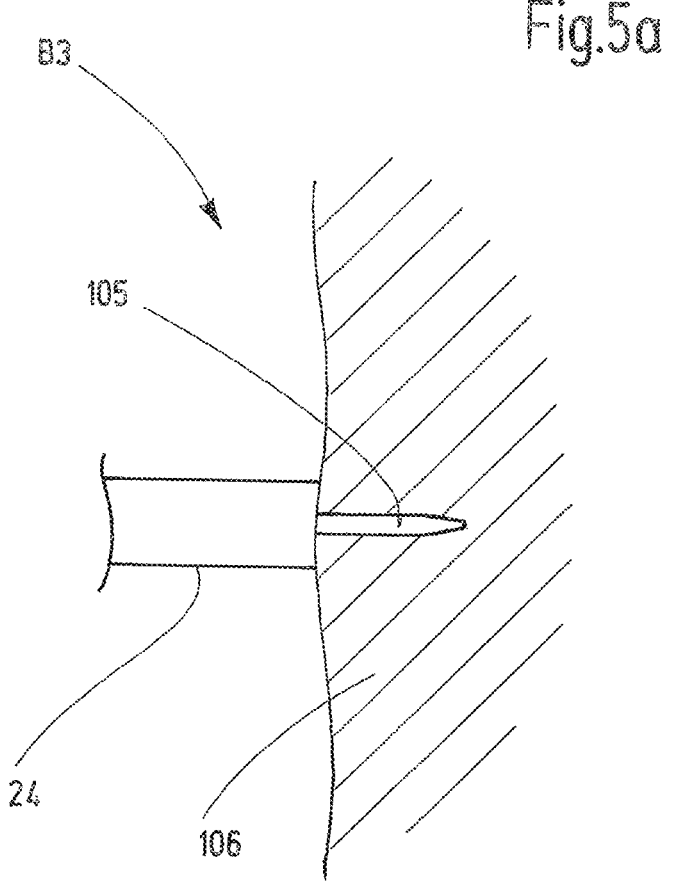

The supply device 101 can be configured to supply a first fluid 16 that can be, e.g. a liquid, particularly a suspension, a solution or the like. This liquid can also be referenced as working liquid, because it serves in a first step for creation of a channel 105 in the tissue 106 on which the instrument 10 is placed as illustrated in FIG. 5b, and in a second step to introduce ingredients of the second fluid in the channel 105. In addition, the supply device 101 supplies a second fluid 17 that comprises ingredients, which shall be deposited in the channel 105 in the tissue 106 of the patient by means of instrument 10 or the system 100 respectively. The ingredients can be, e.g. cells, cell components, pharmaceuticals, radioactive substances for marking or treating or the like. The supply device 101 is in fluid communication with the first conduit 11 and the second conduit 14.

Figure 6:
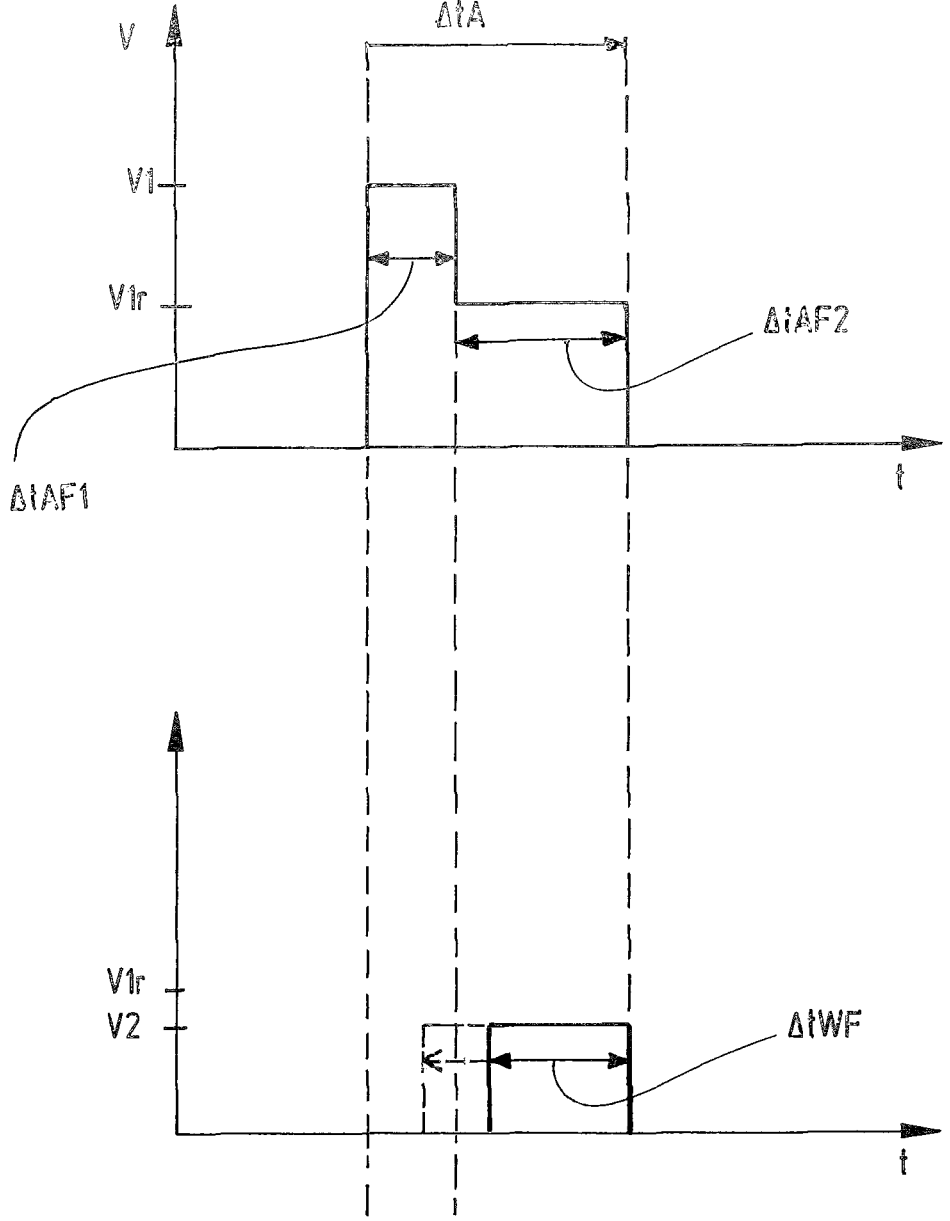

The supply device 101 is configured by means of the control 102 to supply the first fluid 16 and the second fluid 17 in a sequence of supply intervals. The control 102 is preferably configured to control the application system 100 such that within an application time interval $\Delta tA$ that is exemplarily illustrated in FIG. 6 during a first working fluid supply interval $\Delta tAF1$ the first fluid 16 is supplied such that it comprises a first intensity at the first opening 12, particularly a first velocity v1 for forming the channel 105 in the tissue 106. During a second working fluid supply interval $\Delta tAF2$ the control controls the application system 100 such that it comprises at the first opening 12 a reduced first intensity, particularly a reduced first velocity v1r that is smaller than the first intensity or first velocity v1 respectively. In addition, the control 102 is configured to control the application system 100 such that at least in phases during the second working fluid supply interval $\Delta tAF2$ the second fluid 17 is supplied such that it comprises a second intensity or second velocity v2 that is smaller than the reduced first intensity or reduced first velocity v1r. The output of the second fluid 17 next to the first opening 12 in the reacceleration zone 19 in an active ingredients supply interval $\Delta tWF$ can be carried out already during the first working fluid supply interval $\Delta tAF1$ before the change of the intensity or synchronously with the change of the intensity in the first opening 12 or after the change of the intensity. As already mentioned, the change of the intensity is particularly the change of the velocity in the first opening 12 in the axial direction A. The desired second intensity or second velocity v2 of the second fluid 17 on the level of the first opening 12 is obtained amongst other things, because it flows through the ring cross-section of the second conduit 14 that tapers adjacent to the distal end. Upstream of the outer nozzle the second fluid 17 flows with lower velocity that reduces the danger that cells in the second fluid 17 are damaged. The application time interval can have a duration of, e.g. less than 1 second.

The inventive application system 100 or the inventive instrument 10 can be used during operation, e.g. as follows:

In order to minimize the stress of the cells during the application process and still achieve a sufficient penetration depth of the cells, the application process is carried out preferably in at least two steps, as already explained. In a first phase the channel 105 is prepared in the tissue 106. For this in a first working fluid supply interval ΔtAF1 (see FIG. 7), a pilot working jet with high intensity, particularly with high nozzle exit velocity v1 is created. This pilot working jet 20 consists of a working fluid 16, the components of which are insusceptible against mechanical stress, particularly shear stress. Such liquids comprise, e.g. physiological saline solution, a cell culture medium, a gel-like wetting or coating medium for the cells of the second fluid for increasing the mechanical protection and/or the sliding ability or a mixture from one or more of these fluids or liquids. The channel 105 is created in the tissue 106 by means of the pilot working jet 20 in that the pilot working jet 20 mechanically displaces and/or destroys tissue components along the channel to be created. In the second phase in the second working fluid supply interval ΔtAF2 the intensity of the pilot working jet 20 is reduced, particularly the velocity in the first opening down to the reduced first velocity v1r (see FIG. 7). In doing so, also the composition of the first fluid 16 can be changed, particularly by adding of substances or by change of the working fluid. Preferably the composition of the first fluid output from the first opening 12 is similar in the first and second phase. While reducing the intensity, particularly velocity of the pilot working jet 20, the output of the shell jet 21 of cell suspension from the second opening 15 is started. As it is illustrated on the bottom in the scheme in FIG. 7, the start can be prior to the reduction of the intensity of the working jet in the first working fluid supply interval (this is shown in dashed lines at the bottom of FIG. 7), synchronously with the reduction or after the reduction (this is shown at the bottom of FIG. 7 with solid lines). The second fluid 17 can comprise a gel-like wetting or coating medium in addition to the cells in the suspension. During the creation of channel 105 by means of the pilot jet, the second conduit 14 is preferably filled with cell suspension till inside the area in the head 24, in which the first conduit 11 and the second conduit 14 extend coaxially. Preferably the second conduit 14 is nearly completely filled with cell suspension up to a level (measured in the axial direction) of the first opening 12 in order to facilitate a supply of cell suspension in the created channel 105 substantially without delay. This is also a result of the inventive provision of two separate conduits 11, 14 for the first and second fluid and a combination of the first fluid and the second fluid only in the reacceleration zone 19 at the distal end 25 of the instrument 10.

If the cell suspension exits through the outer nozzle and passes the first opening 12 toward the distal end, it surrounds the working jet 20 exiting centrally from the first opening 12 of the inner nozzle formed by the nozzle tube 23 in a shell-like manner, preferably symmetrically. The self-centering of the elastic outer wall section 22 or the outer wall element 29 may support or facilitate that the cell suspension surrounds the working jet 20 in the shell-like manner, preferably symmetrically. In doing so, a uniform loading of the surface of the working jet 20 with cells is achieved by concurrently mainly uniform flow velocity of the second fluid 17. This results in a comparable low interaction of the cells with each other, which facilitates a small cell stress. By means of the instrument 10, the working fluid 16 and the cell suspension are output such that the working fluid jet downstream of the first opening 12 sucks the cell suspension 17 that surrounds working jet 20 in a shell-like manner radial inwardly toward the working jet 20. This is traced back to the Bernoulli effect that also applies in a jet pump and is contrary to the simple mixing of two fluid jets by superimposition. If the working fluid 16 and the cell suspension 17 get into contact with each other, distal from the nozzle tube 23 (particularly as described above by a sucking of the shell jet 21 by the working jet 20) the cells are received by, carried with and accelerated by the working jet until the velocity of the cells corresponds to the velocity of the working jet 20. The small acceleration of the cell suspension 17 in the preacceleration zone 18 in the outer nozzle has the advantage that the cells are only subject to a small shear stress at the radial inward and the radial outward arranged wall surfaces of the outer nozzle that limit the channel in the second conduit 14. But on the other hand, the relative velocity between the cells and the working fluid 20 at the initial contact of the first and second fluid 16, 17 in the reacceleration zone 19 is less than the flow velocity of the working fluid 16. The existing velocity difference of the two liquids 16, 17 in this area, in which these fluids get into contact for the first time, indeed leads to the creation of shear stress of the cells, however, in total a small cell stress is achieved and thus a high survival rate of the cells during the injection into the channel 105 in the tissue 106.

The present invention additionally improves the survival of the cells due to the change adjacent to the distal end of the instrument 10 from channels extending next to each other, particularly parallel, to the coaxially extending channels of the first and second conduit 11, 14. Also due to following an approach with the invention for outside mixing in that the instrument 10 receives the first fluid 16 and the cell comprising a second fluid 17 via conduits 11, 14 and that the addition of the cell suspension 17 or cells in the working jet 20 is only carried out after the passage through the first nozzle tube 23, a high survival rate of the cells is improved. A second nozzle formed by the outer surface of the nozzle tube 23 and the inner surface of the outer wall section 22 or the outer wall element 29, as illustrated in FIG. 1 or 2, provides a particular low shear flow configuration and is thus supporting for a high survival rate of the cells by the continuous tapering at least of the inner diameter of the elastic outer wall element 29.

The transport of the cell suspension 17 or the cell ingredients by the working jet 20 is facilitated, if the distal end of the first nozzle tube 23 is offset away from the distal end of the elastic outer wall element 29, as exemplarily illustrated in FIGS. 1 and 2. The reacceleration zone 19 in which a mixing occurs is thus surrounded in axial sections from the elastic outer wall element 29, more precisely from the cylindrical section 29c. The shape of the outer wall element 29 and the arrangement of the outer wall element 29 and the nozzle tube 23 have the advantage that the shell jet 21, particularly due to the section 29c, is steadily approached closely to the nozzle tube 23 and finally to the central working jet 20 and indeed preferably substantially such that the shell jet 21 and the working jet 20 have predominantly the same direction components. The distal end of the nozzle tube 23 that forms the first opening 12 can be offset back relative to the distal end of the elastic outer wall section 29 that forms the second opening 15, e.g. by 0.5 to 3 mm. In a particularly preferred embodiment the nozzle tube 23 is offset back by 1 mm. Due to this offset of the first opening 12 at the distal face 13 of the first conduit, from the distal end 25 of the instrument 10 a minimum length of the reacceleration zone 19 in which also the reception of ingredients of the second fluid 17 in the first first fluid 16 occurs, is defined inside the instrument 10. The reacceleration zone 19 is also mainly free, if the distal end 25 of the instrument 10 is pressed on the tissue 106.

If the distal end 25 of the instrument 10 is pressed slightly on the tissue surface, it can be achieved that the position of the distal end 25 of the instrument 10 and particularly of the first nozzle tube 23 is not changed during creation of channel 105 and the application of the cells. For this the exemplary embodiment of the instrument 10 according to FIG. 2 comprises a cap 34 of a material that is compression resistant in the axial direction A and is bending resistant, wherein the cap 34 impedes that tissue reaches and deforms the elastic outer wall element 29 when the instrument is placed on the tissue.

An application process comprises a needleless creation of an injection channel 105 in the tissue 106 in a target area by means of the instrument 10 and the injection of cell suspension in a predefined dosage into the channel 105. The application process can in addition comprise the subsequent sealing of the injection channel 105, e.g. by means of a sealing medium additively mixed the working fluid jet 20 subsequently to adding the cell suspension 17 via the second conduit 14 to the working fluid jet 20. The added sealing medium can have a higher viscosity than the cell suspension. The sealing medium can be gel-like.

In order to guarantee higher efficiency of a substance introduced in a tissue of a patient, e.g. in order to guarantee a high integrity of cells introduced in the tissue of a patient, according to the invention an instrument 10 with a first conduit 11 for emitting a first fluid 16 from a first opening 12 of the first conduit 11 in the axial direction A into a reacceleration zone 19 and with a second conduit 14 for channeling of a second fluid 17 in the reacceleration zone 19 in the axial direction A is provided such that active ingredient components, e.g. cells, of the second fluid 17 are reaccelerated in the axial direction as a result of the flow in the reacceleration zone 19 by means of the first fluid 16 that enters the reacceleration zone 19. A coaxial configuration of the first and the second conduit 11, 14 is preferred, because in doing so, around the first opening 12 a shell jet 21 of second fluid 17 can be created that flows downstream in the axial direction around the central working jet 20. In addition, a head 24 for an inventive instrument 10 and an application system 100 with an inventive instrument 10 is provided. In exemplary, not illustrated embodiments of the instrument, the instrument can comprise multiple second conduits, i.e. at least two second conduits. With the multiple second conduits similar or different second fluids can be channeled in the reacceleration zone in an alternate manner and/or at least during phases concurrently. In doing so, ingredients of the second fluids can be reaccelerated in the axial direction due to the flow into the reacceleration zone by the first fluid that enters the reacceleration zone in the axial direction. For example, the second fluids can be different substances or can comprise different substances, e.g. different active ingredients. Alternatively or additionally, embodiments of the inventive instrument can also comprise multiple first conduits, e.g. at least two first conduits that are configured to output similar or different first fluids in the reacceleration zone in order to reaccelerate one or more second fluids.

The invention claimed is:

1. An instrument comprising:
a nozzle having a first section defined by a first interior cross-sectional diameter and a nozzle opening, and a second section defined by an interior diameter greater than the first interior cross-sectional diameter and having an interior conical shape; and
a tube within the nozzle extending from the second section of the nozzle into the first section of the nozzle, the tube comprising a cylindrical end with an opening that opens within the first section of the nozzle upstream from the nozzle opening of the first section, whereby
an area extending from the opening of the cylindrical end of the tube and the nozzle opening of the first section defines a reacceleration zone,
the tube is configured to deliver a first fluid in an axial direction of the instrument to the reacceleration zone at a first velocity sufficient to form a channel in a tissue,
the second section of the nozzle configured to accelerate a flow of a second fluid upstream from the reacceleration zone and to deliver the second fluid to the reacceleration zone,
wherein the reacceleration zone is fluidically connected to both an inside of the tube and the second section of the nozzle at a same time.

2. The instrument of claim 1, wherein:
the second section of the nozzle defines a preacceleration zone upstream of the reacceleration zone,
the instrument is configured to preaccelerate the second fluid in the axial direction of the instrument in the preacceleration zone, and
the opening of the cylindrical end of the tube opens into the reacceleration zone such that the tube is configured to output the first fluid into the reacceleration zone to reaccelerate the second fluid in the axial direction of the instrument.

3. The instrument of claim 1, wherein:
the nozzle concentrically surrounds the tube at the opening of the cylindrical end of the tube, and
the nozzle being configured to direct the flow of the second fluid around the first fluid in a ring-shaped shell jet when the first fluid exits from the opening of the cylindrical end of the tube and the second fluid exits the second section of the nozzle.

4. The instrument of claim 1, wherein the nozzle further comprises a wall that is elastic.

5. The instrument of claim 1, further comprising:
a centering device arranged radially between the tube and the nozzle.

6. The instrument of claim 1, wherein the instrument is configured to channel the first fluid and the second fluid adjacent to each other until the first fluid and the second fluid reach a transition location and to channel the first fluid and the second fluid coaxially after the transition location.

7. The instrument of claim 1, wherein the instrument is configured to inject ingredients within the second fluid into the tissue in a needleless manner.

8. The instrument of claim 1, wherein the tube comprises the first fluid therein, the second section comprises the second fluid therein, and the reacceleration zone comprises both the first fluid and the second fluid therein.

9. An application system comprising:
the instrument according to claim 1; and
a supply device that is in fluid connection with the tube and the nozzle and configured to supply the first fluid and the second fluid in a sequence of supply intervals, wherein the sequence of supply intervals comprises a first working supply interval and a second working supply interval.

10. The application system of claim 9, wherein the supply device is configured to:

supply the first fluid to the opening of the cylindrical end of the tube at the first velocity during the first working fluid supply interval, supply the first fluid to the opening of the cylindrical end of the tube at a second velocity that is less than the first velocity during the second working fluid supply interval, and supply the second fluid to the reacceleration zone, via the nozzle, at a velocity that is less than the second velocity of the first fluid during at least a portion of the second working fluid supply interval.

11. The application system of claim 9, wherein the supply device is configured to:

supply the first fluid to the opening of the cylindrical end of the tube at the first velocity during the first working fluid supply interval, supply the first fluid to the opening of the cylindrical end of the tube at a second velocity that is equal to the first velocity during the second working fluid supply interval, and supply the second fluid to the reacceleration zone, via the nozzle, at a third velocity that is less than the second velocity of the first fluid during at least a portion of the second working fluid supply interval.

12. The application system of claim 9, wherein the supply device and the instrument are configured to preaccelerate the second fluid upstream from the reacceleration zone to a second velocity that is less than the first velocity of the first fluid.

13. The application system of claim 9, wherein the supply device and the instrument are configured to preaccelerate a cell suspension within the second fluid upstream from the reacceleration zone to a second velocity that is less than the first velocity of the first fluid.

* * * * *